United States Patent
Suzuki et al.

(10) Patent No.: US 9,833,147 B2
(45) Date of Patent: Dec. 5, 2017

(54) MAMMOGRAPHY DEVICE

(71) Applicant: HAMAMATSU PHOTONICS K.K., Hamamatsu-shi, Shizuoka (JP)

(72) Inventors: Toshihiko Suzuki, Hamamatsu (JP); Yutaka Yamashita, Hamamatsu (JP); Yukio Ueda, Hamamatsu (JP); Etsuko Yamaki, Hamamatsu (JP); Daisuke Yamashita, Hamamatsu (JP); Kenji Yoshimoto, Hamamatsu (JP); Harumi Sakahara, Hamamatsu (JP); Hiroyuki Ogura, Hamamatsu (JP); Hatsuko Nasu, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 251 days.

(21) Appl. No.: 14/361,428

(22) PCT Filed: Nov. 9, 2012

(86) PCT No.: PCT/JP2012/079120
§ 371 (c)(1),
(2) Date: May 29, 2014

(87) PCT Pub. No.: WO2013/080773
PCT Pub. Date: Jun. 6, 2013

(65) Prior Publication Data
US 2014/0357998 A1  Dec. 4, 2014

(30) Foreign Application Priority Data
Dec. 2, 2011 (JP) ................................. 2011-264891

(51) Int. Cl.
*A61B 5/00* (2006.01)
*A61B 8/08* (2006.01)
(Continued)

(52) U.S. Cl.
CPC .......... *A61B 5/0091* (2013.01); *A61B 5/0035* (2013.01); *A61B 5/708* (2013.01);
(Continued)

(58) Field of Classification Search
CPC .................................................... A61B 5/0091
See application file for complete search history.

(56) References Cited

U.S. PATENT DOCUMENTS 6,130,958 A   10/2000  Rohler et al.
7,886,782 B1   2/2011  Curtis
(Continued)

FOREIGN PATENT DOCUMENTS

CN   101511263   8/2009
CN   101541236   9/2009
(Continued)

OTHER PUBLICATIONS

Jacqueline E. Gunther et al., "Predicting Tumor Response in Breast Cancer Patients Using Diffuse Optical Tomography," SPIE Digital Library, Web, 2017.
(Continued)

*Primary Examiner* — Rochelle Turchen
(74) *Attorney, Agent, or Firm* — Drinker Biddle & Reath LLP

(57) ABSTRACT

A mammography device is disclosed. The mammography device includes a container configured to surround the breast and a plurality of optical fibers attached to be directed inward in the container and configured to perform radiation and detection of light. The container has a base member having an opening, a plurality of annular members continuously disposed to come in communication with the opening, and a bottom member disposed inside the annular member spaced the farthest distance from the base member. The annular members and the bottom member are configured to relatively displace the adjacent annular member on the side of the base member or the base member in a communication direction. Some of the plurality of optical fibers is attached to the plurality of annular members.

9 Claims, 14 Drawing Sheets

(51) Int. Cl.
*A61B 8/00* (2006.01)
*G01N 21/47* (2006.01)

(52) U.S. Cl.
CPC .......... *A61B 8/0825* (2013.01); *A61B 8/4416* (2013.01); *A61B 2562/046* (2013.01); *A61B 2562/146* (2013.01); *A61B 2562/168* (2013.01); *G01N 21/4795* (2013.01); *G01N 2021/4797* (2013.01); *G01N 2201/0826* (2013.01); *G01N 2201/0833* (2013.01)

(56) References Cited

U.S. PATENT DOCUMENTS

| 2004/0097810 | A1 | 5/2004 | Miwa | |
|---|---|---|---|---|
| 2010/0073674 | A1* | 3/2010 | Yoshida | A61B 5/0073 356/300 |
| 2014/0236003 | A1* | 8/2014 | Hielscher | A61B 5/0091 600/428 |

FOREIGN PATENT DOCUMENTS

| JP | 2002-272745 | 9/2002 |
|---|---|---|
| JP | 2008-099810 A | 5/2008 |
| JP | 2008-101992 A | 5/2008 |
| JP | 2009-516561 | 4/2009 |
| JP | 2009-189726 A | 8/2009 |
| WO | WO 03/099101 | 12/2003 |

OTHER PUBLICATIONS

Jacqueline E. Gunther et al., "Diffuse Optical Tomography Imaging System for Monitoring Breast Tumor Response to Neoadjuvant Chemotherapy," Biomedical Optics and 3D Imaging OSA, 2012.

* cited by examiner

1

MAMMOGRAPHY DEVICE

TECHNICAL FIELD

The present invention relates to a mammography device.

BACKGROUND ART

In Patent Literatures 1 and 2, a mammography device for acquiring internal information of breasts of an examinee by radiating light to the breasts and detecting diffused light is disclosed. The device disclosed in Patent Literatures 1 and 2 includes a container configured to surround the breast, and a plurality of optical fibers disposed to face inward in the container to perform radiation and detection of light.

CITATION LIST

Patent Literature

[Patent Literature 1] Japanese Unexamined Patent Application Publication No. 2008-099810
[Patent Literature 2] Japanese Unexamined Patent Application Publication No. 2009-189726

SUMMARY OF INVENTION

Technical Problem

In a general mammography (breast imaging) apparatus currently in wide use, in order to inspect for breast cancer or the like, an X-ray is radiated while breasts of an examinee are pressed and the transmitted X-ray is imaged, acquiring internal information of the breasts. However, since an influence exerted on the breasts and the breast cancer by radiation of the X-ray is worrisome, in recent years, a method of acquiring internal information of the breasts by radiating light from a plurality of positions to the breasts of the examinee and detecting intensity of the diffused light at the plurality of positions is being researched.

In this type of mammography device, the inventor(s) found the following problems. That is, while shapes and sizes (volumes) of breasts of examinees are different from each other, when a position of an optical fiber at which radiation of light to breasts of an examinee and detection of the diffused light is performed is fixed, an amount of light entering the breast differs according to whether the breast has a large or small volume, and a difference in precision of internal information occurs.

The above-mentioned problems will be described in detail. FIG. 12 is a cross-sectional view showing a configuration of a mammography device disclosed in Patent Literature 1 in the vicinity of a container. A mammography device 100 includes an inner container 103 configured to surround a breast B, an outer container 104 disposed outside the inner container 103 so as to form a gap 105 with the inner container 103, a partition wall 106 configured to divide the gap 105 into an inflow chamber 105a and a discharge chamber 105b, a plurality of optical fibers 107 disposed to face inward in the inner container 103 and configured to perform radiation and detection of light, a pipe 109 configured to inject a liquefied interface agent 108 into the inflow chamber 105a, and a pipe 110 configured to discharge an interface agent 108 from the discharge chamber 105b. Further, the interface agent 108 is a liquid having substantially the same optical coefficient as a biological tissue, and fills the gap between the inner container 103 and the breast B in order to harmonize an optical coefficient such as a light absorption coefficient, a light scattering coefficient, or the like, between a fiber end of the optical fiber 107 disposed at a container inner surface and the breast B with the breast B through the inner container 103. Accordingly, a boundary condition matching an inner shape of the inner container 103 is used to construct a reconstructed image.

In the mammography device 100 including the above-mentioned configuration, light radiated from a certain optical fiber 107 enters the breast B, is diffused, and then enters another optical fiber 107 to be detected. Here, FIG. 13 is a view showing a situation of propagation of light when a volume of the breast B is large, and FIG. 14 is a view showing a situation of propagation of light when a volume of the breast B is small. As shown in FIG. 13, when the volume of the breast B is large, since the breast B is close to each of the optical fibers 107, most of light P radiated from the optical fiber 107 enters the breast B. Then, the light P is diffused in the breast B and then emitted from the breast B to enter the other optical fiber 107.

Meanwhile, as shown in FIG. 14, when the volume of the breast B is small, since the breast B is separated from each of the optical fibers 107, most of the light P radiated from the optical fiber 107 propagates only the interface agent 108 without entering the breast B. Then, the light P is diffused in the interface agent 108 and then enters the other optical fiber 107. Accordingly, in comparison with the case shown in FIG. 13, internal information of the breast B included in the detected diffused light is reduced, and precision of the finally obtained internal information is decreased. Such a decrease in precision of the internal information may be represented as, for example, a decrease in resolution of the reconstructed image.

In consideration of the above-mentioned problems, the present invention is directed to provide a mammography device capable of reducing an influence on precision of internal information due to a difference in a shape or a size (volume) of a breast.

Solution to Problem

In order to solve the above-mentioned problem, a mammography device according to an aspect of the present invention is a mammography device for acquiring internal information of a breast of an examinee by radiating light to the breast and detecting the diffused light. The mammography device includes a container configured to surround the breast, and a plurality of optical fibers attached to the container to be directed inward in the container and configured to perform radiation and detection of light. The container has a base member having an opening through which the examinee inserts the breast, a plurality of annular members continuously disposed at an opposite side of the examinee to come in communication with the opening, and a bottom member disposed inside the annular member spaced the farthest distance from the base member among the plurality of annular members. An inner diameter of each of the annular members is smaller than that of the adjacent annular member on the side of the base member or that of the opening of the base member, and the annular members and the bottom member are configured to be relatively displaced in a communication direction with respect to the adjacent annular member on the side of the base member or the base member. At least some of the plurality of optical fibers is attached to the plurality of annular members.

In the mammography device according to the aspect, the container to which the plurality of optical fibers are attached has the plurality of annular members and the bottom member, and the annular members and the bottom member are configured to be relatively displaced in the communication direction with respect to the adjacent member (the base member or the annular member) on the side of the base member. According to the above-mentioned configuration, an inner capacity of the container can be varied to match a shape or size (volume) of the breast of the examinee. In addition, since at least some of the plurality of optical fibers is attached to the plurality of annular members, positions of the plurality of optical fibers are also varied with displacement of the plurality of annular members. Accordingly, a variation in distance between the plurality of optical fibers and the breast due to a difference in shape or size of the breast can be suppressed, and the amount of light entering the breast can be maintained to a certain amount regardless of the size of the breast. Accordingly, according to the mammography device, an influence on precision of the internal information due to the difference in shape or size of the breast can be reduced.

In the mammography device, the base member, the plurality of annular members and the bottom member have surfaces opposite to the base member, the annular member or the bottom member adjacent thereto and extending in the communication direction. As described above, in the mammography device, the gap between the container and the breast may be filled with a liquefied interface agent. In this case, as the base member, the plurality of annular members and the bottom member have surfaces opposite to the base member, the annular member or the bottom member adjacent thereto and extending in the communication direction respectively, the neighboring members are adhered to prevent generation of the gap upon displacement of the plurality of annular members.

In the mammography device, seal members may be installed between the base member and the annular member adjacent to the base member, between the neighboring annular members, and between the bottom member and the annular member adjacent to the bottom member. As the seal members are installed between the surfaces, leakage of the interface agent from the container can be appropriately prevented.

The mammography device may further include a control unit configured to control displacement in the communication direction of the plurality of annular members and the bottom member, and the control unit may continuously vary a distance from the opening of the base member to the bottom member. Accordingly, since an inner capacity of the container is finely varied to match the various shapes and sizes of the breast, an influence on precision of the internal information due to the difference in the shape or size of the breast can be further reduced.

The mammography device may further include a control unit configured to control displacement in the communication direction of the plurality of annular members and the bottom member, and the control unit may vary a distance from the opening of the base member to the bottom member in a plurality of predetermined steps. In the mammography device, when the internal information of the breast is acquired based on the detected diffused light from the breast, a reconstructed image can be calculated from a boundary condition of the container inner surface. In this case, when the capacity of the container is finely varied according to the examinee, the boundary condition should be calculated every time, and calculation of the reconstructed image takes a long time. On the other hand, like the above-mentioned mammography device, as the control unit varies a distance from the opening of the base member to the bottom member in the plurality of predetermined steps, since the boundary condition is limited to a plurality of predetermined conditions, it is not necessary to calculate the boundary condition at every measurement, and the calculation time of the reconstructed image can be reduced.

The mammography device may further include an ultrasonic wave probe disposed to face inward in the container and configured to scan ultrasonic waves toward the breast and receive the reflected waves from the breast. Accordingly, the ultrasonic wave image of the breast is drafted, the distance from the opening of the base member to the bottom member (i.e., the capacity of the container), or disposition or capacity of the breast in the container can be previously checked, and the size of the container can be complexly optimized to match the shape or size of the breast. Accordingly, intensity of the signal from the breast measured by the light is substantially equalized regardless of the size of the breast, and deviation between the reconstructed images can be reduced. Further, as the reconstructed image obtained by the optical measurement and the ultrasonic wave image are combined, a diagnosis image having a larger amount of information can be provided.

When the mammography device includes a probe, the probe may be attached to the bottom member. Accordingly, the ultrasonic wave can be radiated from a front surface of the breast, and the ultrasonic wave image can be appropriately drafted.

In the mammography device, some of the plurality of optical fibers may be attached to the bottom member. In addition, some of the plurality of optical fibers may be attached to the opening of the base member. In this way, as some of the plurality of optical fibers are also attached to the members other than the plurality of annular members, the plurality of optical fibers can be evenly disposed around the breast, and precision of the internal information can be further increased.

In the mammography device, the plurality of optical fibers may be disposed at the plurality of annular members in parallel in a circumferential direction, and attachment angles of the plurality of optical fibers with reference to the communication direction may differ with respect to each of the plurality of annular members. Accordingly, the light can be precisely radiated toward the breast at an angle according to the attachment position of the optical fiber.

Advantageous Effects of Invention

According to the mammography device in accordance with one aspect of the present invention, an influence due to a difference in a shape or a size (a volume) of a breast can be reduced.

DESCRIPTION OF EMBODIMENTS

Figure 1:
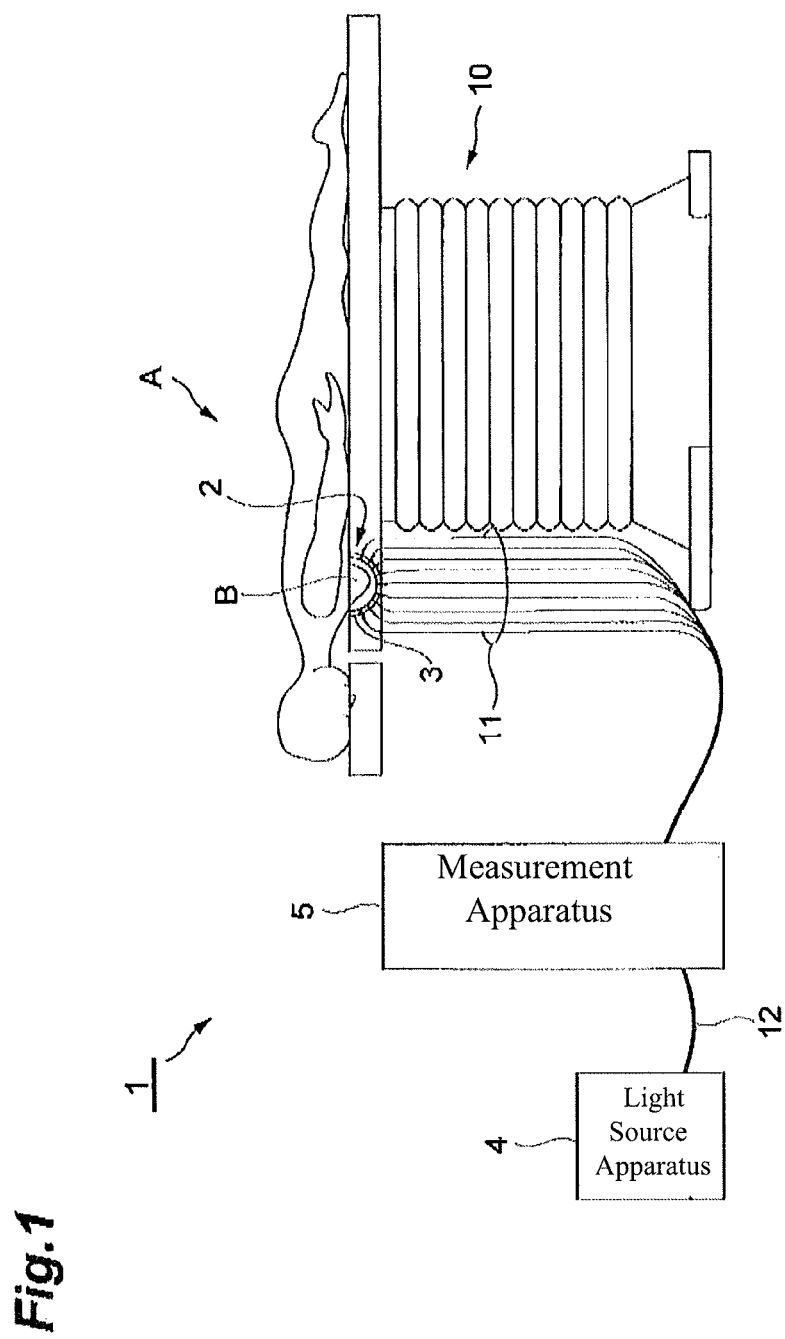
FIG. 1 is a view showing the entire configuration of an embodiment of a mammography device.

Hereinafter, an embodiment of a mammography device according to the present invention will be described in detail with reference to the accompanying drawings. Further, the same components in the description of the drawings are designated by the same reference numerals, and overlapping description thereof will be omitted.

FIG. 1 is a view showing the entire configuration of an embodiment of a mammography device. A mammography device 1 according to the embodiment is an apparatus for acquiring internal information of a breast B of an examinee A by radiating light to the breast B and detecting diffused light (returned light), and inspecting whether there is a tumor, cancer, or the like, based on the internal information. Referring to FIG. 1, a bed (a base) 10 on which the examinee A lies face down is installed at the mammography device 1, and a hemispherical container 3 (a measurement cup) configured to surround the breast B hanging down from the examinee A is attached to the bed 10. One ends of a plurality of optical fibers 11 configured to radiate and detect light are fixed to the container 3 and directed inward in the container 3 to configure a measurement unit (a gantry) 2. The mammography device 1 includes a light source apparatus 4 configured to generate pulse light radiated into the container 3, and a measurement apparatus 5 configured to calculate internal information of the breast B based on the light emitted from the light source apparatus 4 and the diffused light after radiation. The other ends of the plurality of optical fibers 11 are optically connected to the measurement apparatus 5, and the light source apparatus 4 and the measurement apparatus 5 are optically connected to each other via the optical fibers 12. The light source apparatus 4 and the measurement apparatus 5 may be connected to each other in a time alignment manner via electric cables.

Figure 2:
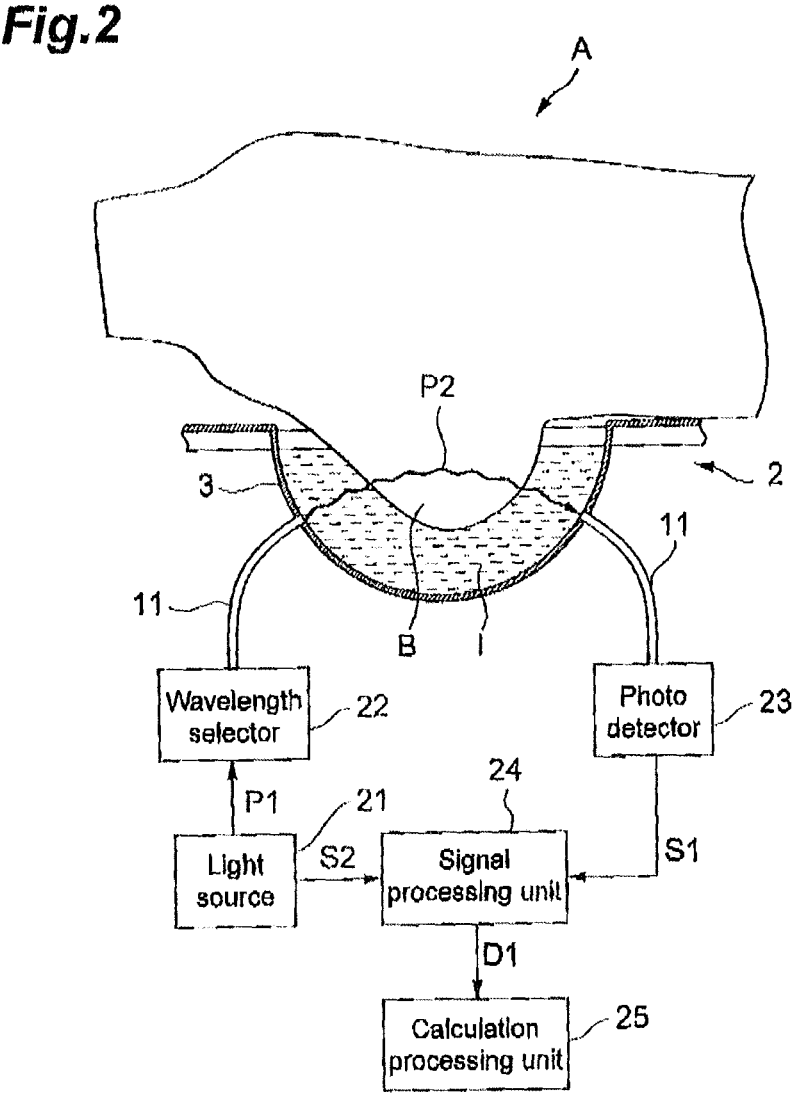
FIG. 2 is a block diagram showing a functional configuration of the mammography device.

FIG. 2 is a block diagram showing a functional configuration of the mammography device 1. In FIG. 2, for the convenience of description, among the plurality of optical fibers 11, only one fiber for radiation and only one fiber for detection are representatively shown, and the other optical fibers 11 are not shown. As shown in FIG. 2, the mammography device 1 includes a light source 21, a wavelength selector 22, a photo detector 23, a signal processing unit 24, and a calculation processing unit 25. Among these, the light source 21 and the wavelength selector 22 are installed in, for example, the light source apparatus 4. The photo detector 23, the signal processing unit 24 and the calculation processing unit 25 are installed in, for example, the measurement apparatus 5.

The light source 21 is an apparatus for generating pulse light P1. Pulse light having a short time width such that internal information of the living body can be measured is used as the pulse light P1, and conventionally, for example, a time width having a range of 1 ns or less is selected. The pulse light P1 generated from the light source 21 is input into the wavelength selector 22. Various light sources such as a light emitting diode, a laser diode, various pulse diodes, and so on, may be used as the light source 21.

The wavelength selector 22 is an apparatus for selecting a wavelength of the pulse light P1 input from the light source 21 to a predetermined wavelength. A wavelength selected by the wavelength selector 22 may be a wavelength of a near-infrared light region of about 700 to 900 nm from a relation between permeability of the living body and spectral absorption coefficient of an absorption element to be quantified. However, the selected wavelength is not limited to this region. Pulse light P2 having a wavelength selected by the wavelength selector 22 enters the optical fiber 11 for optical radiation. According to necessity, for example, when internal information of a plurality of elements is measured, or the like, the light source 21 and the wavelength selector 22 are configured to input pulse light having a plurality of wavelength elements as measurement light. When the wavelength selection is not needed, installation of the wavelength selector 22 may be omitted.

The optical fiber 11 for optical radiation receives the pulse light P2 from the wavelength selector 22, and radiates the pulse light P2 from an end surface thereof with respect to the breast B in the container 3, The end surface of the optical fiber 11 is disposed at a predetermined optical radiation position in an inner wall of the container 3. The optical fiber 11 for optical detection inputs the diffused light of the pulse light P2 emitted from the breast B from one end surface thereof, and outputs the diffused light to the photo detector 23. The end surface of the optical fiber 11 is disposed at a predetermined optical detection position in an inner wall of the container 3. A gap between the inner wall of the container 3 and the breast B is filled with an interface agent I. The interface agent I is a liquid having substantially the same optical coefficient, such as a light scattering coefficient or the like, as the biological tissue.

The photo detector 23 is an apparatus for detecting light input from the optical fiber 11 for optical detection. The photo detector 23 generates an optical detection signal S1 showing luminous intensity or the like of the detected light. The generated optical detection signal S1 is input into the signal processing unit 24. Various devices such as a photo diode, an avalanche photo diode, a PIN photo diode, or the like may be used as the photo detector 23 in addition to a photo-multiplier tube (PMT). The photo detector 23 may have spectral sensitivity characteristics that can sufficiently detect the light having a wavelength of the pulse light P2. When the diffused light from the breast B is minute, a photo detector having high sensitivity or high gain may be used.

The signal processing unit 24 is a means electrically connected to the photo detector 23 and the light source 21, and configured to acquire a measurement waveform showing a time variation of the luminous intensity of the diffused light based on the optical detection signal S1 detected by the photo detector 23 and a pulse light emission trigger signal S2 from the light source 21. The signal processing unit 24 holds information of the acquired measurement waveform as electronic data, and provides the electronic data D1 to the calculation processing unit 25.

The calculation processing unit 25 is a means electrically connected to the signal processing unit 24, and is configured to input the electronic data D1 from the signal processing unit 24 and calculate internal information of the breast B using information of the measurement waveform included in the electronic data D1. The internal information includes, for example, a scattering coefficient and absorption coefficient in the breast B, and concentrations of elements contained in the breast B. Calculation of the internal information is performed by applying, for example, analysis calculation through time resolved spectroscopy (TRS) using a time-resolved waveform of the detected light, phase modulation spectroscopy (PMS) using modulated light, or the like. The calculation processing unit 25 may further have a function of controlling the above-mentioned components such as the light source 21, the photo detector 23, or the like. The calculation processing unit 25 is realized by, for example, a computer having a calculation means, referred to as a central processing unit (CPU), and a storage means such as a memory or the like.

In FIG. 2, while each of the optical fiber 11 for optical radiation and the optical fiber 11 for optical detection has been representatively described, in the mammography device 1 of the embodiment, for example, the plurality of (20 or more) optical fibers 11 are used, and the end sections of these are disposed at predetermined positions in the inner surface of the container 3. Then, some of the optical fibers 11 are used for optical radiation, and the other optical fibers 11 are used for optical detection. Alternatively, the optical fibers 11 may have both functions of optical radiation and optical detection. For example, each of the optical fibers 11 has a dual core. As light is radiated from one core and light is detected by the other core, the optical fiber 11 can be appropriately realized.

Figure 3:
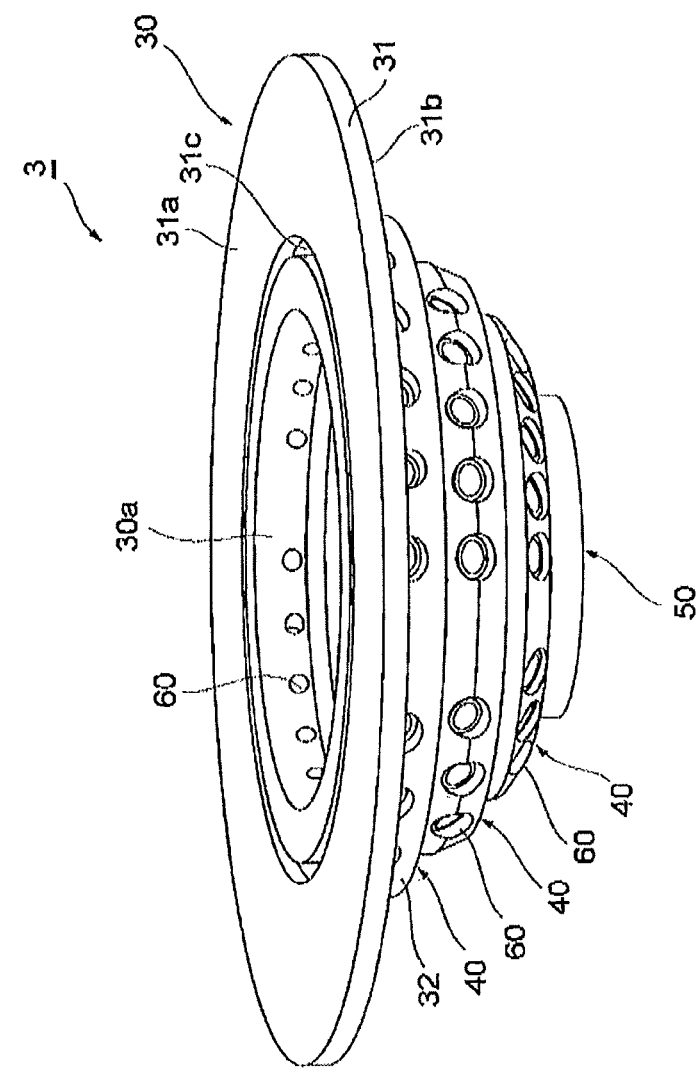
FIG. 3 is a perspective view when seen from a diagonal upper side of a container.
Figure 4:
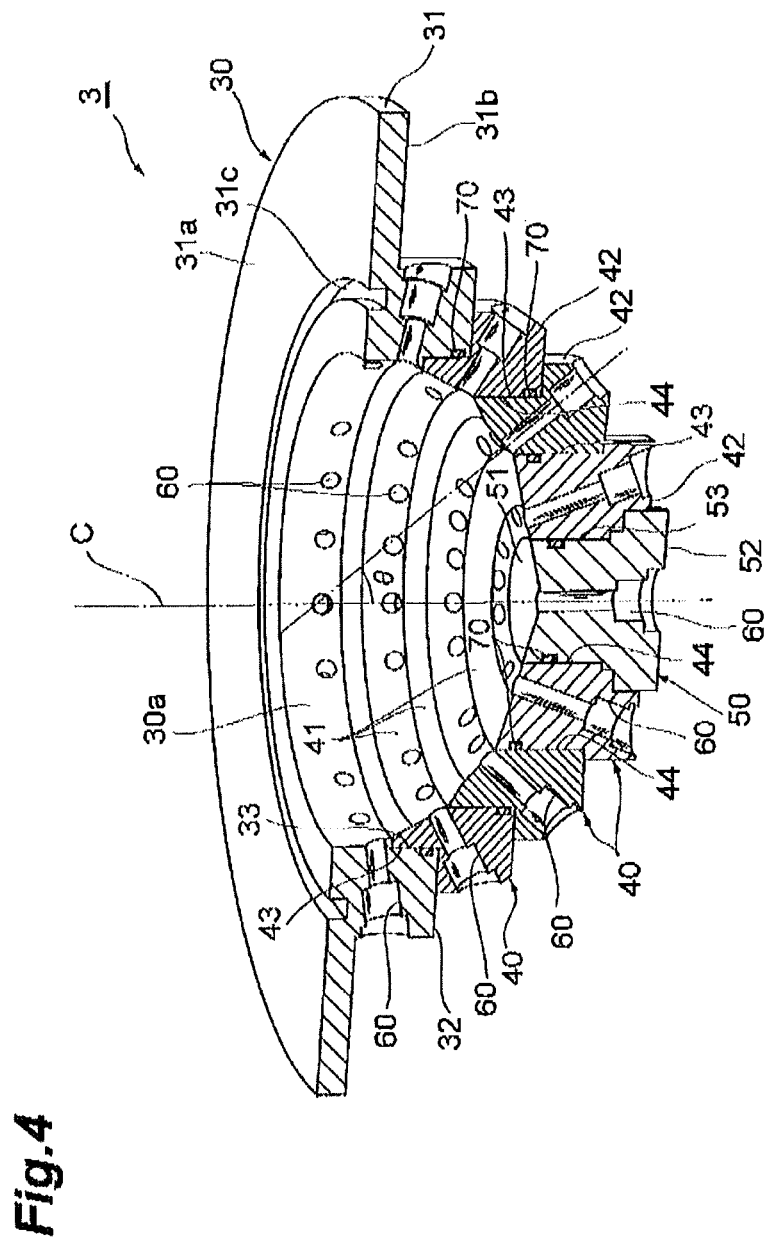
FIG. 4 is a cut-away perspective view showing a situation in which the container is cut in a breast insertion direction.

FIG. 3 is a perspective view of the container 3 of the embodiment when seen from a diagonal upper side. FIG. 4 is a cut-away perspective view showing a situation in which the container 3 is cut in a breast insertion direction. As shown in FIGS. 3 and 4, the container 3 has a base member 30, a plurality of (in the drawings, 3) annular members 40 (measurement rings), and a bottom member 50 (a measurement center flange). In FIGS. 3 and 4, for the convenience of understanding, the plurality of optical fibers 11 attached to the container 3 are not shown, and a plurality of through-holes 60 through which the plurality of optical fibers 11 are fixed are shown.

The base member 30 is a member attached to the bed 10 shown in FIG. 1. The base member 30 includes a substantially annular plate-shaped section 31 having a surface 31a in contact with the examinee A and a rear surface 31b opposite to the examinee A. The base member 30 includes an annular section 32 installed at the rear surface 31b side of the plate-shaped section 31. The plate-shaped section 31 and the annular section 32 have a substantially circular opening 30a through which the examinee A inserts the breast B. An inner circumferential surface of the opening 30a configures a portion of the inner surface of the container 3. The plurality of through-holes 60 through which the optical fibers 11 are fixed are formed at the annular section 32 and directed inward in the opening 30a. The plurality of through-holes 60 are formed in a circumferential direction of the annular section 32 in parallel at substantially equal intervals, and thus the plurality of optical fibers 11 are disposed in the circumferential direction of the annular section 32 in parallel at substantially equal intervals. The base member 30 further has a circular groove 31e formed around the opening 30a in the surface 31a. The circular groove 31c catches the interface agent I that overflows from the gap between the container 3 and the breast B during the measurement. The interface agent Y is suctioned by a suction pump (not shown) connected to the circular groove 31c. As the base member 30 has the circular groove 31c, contamination of a periphery of the opening 30a by the interface agent I can be prevented.

The plurality of annular members 40 are disposed with respect to the base member 30 at an opposite side of the examinee A (i.e., near the rear surface 31b), and continuously disposed (with no gap) in an axis C direction perpendicular to an opening surface of the opening 30a to come in communication with the opening 30a of the base member 30. The plurality of annular members 40 have inner circumferential surfaces 41 that form a portion of the inner surface of the container 3, and outer circumferential surfaces 42 that form a portion of the outer surface of the container 3. An inner diameter of the annular member 40 in vicinity of the base member 30 is smaller than that of the opening 30a of the base member 30. In addition, an inner diameter of another annular member 40 is smaller than that of the annular member 40 in the vicinity of the base member 30. In this way, as the annular member 40 is spaced apart from the base member 30, the inner diameter is reduced. Accordingly, the inside of the container 3 may have a substantially hemispherical shape.

The plurality of through-holes 60 are formed in the annular members 40. The plurality of through-holes 60 of the annular members 40 are formed to pass through the inner circumferential surface 41 from the outer circumferential surface 42, and extend in an inward direction in the container 3. The plurality of through-holes 60 are formed in a circumferential direction of the annular member 40 in parallel at substantially equal intervals, and thus the plurality of optical fibers 11 are disposed in the circumferential direction of the annular member 40 at substantially equal intervals.

When the reconstructed image is calculated, the inner surface of the container 3 defines a boundary condition. For this reason, a shape or an inclination angle of the inner circumferential surfaces 41 of the plurality of annular members 40 are set to match an appropriate boundary condition. In order to precisely radiate light toward the breast B at an angle according to attachment positions of the plurality of optical fibers 11, the attachment angles of the plurality of optical fibers 11 with reference to a communication direction (i.e., the axis C direction) of the plurality of annular members 40 differ from each other according to the plurality of annular members 40. For this reason, as shown in FIG. 4, angles in the central axis direction of the plurality of through-holes 60 with reference to the axis C direction (an angle θ of one of the through-holes 60 is shown in FIG. 4) also differ from each other according to the plurality of annular members 40. For example, in the embodiment, as a distance from the base member 30 to the annular member 40 is increased, an angle formed by the axis C and the central axis direction of the through-hole 60 (i.e., the optical axis direction of the optical fiber 11) is gradually reduced.

The bottom member 50 is disposed inside the annular member 40 at one farthest from the base member 30 among the plurality of annular members 40, and closes an opening formed by the inner circumferential surfaces 41 of the annular members 40. The bottom member 50 has an upper surface 51 that forms a portion of the inner surface of the container 3, and a lower surface 52 that forms a portion of the outer surface of the container 3. One through-hole 60 is formed in the bottom member 50. The through-hole 60 of the bottom member 50 is formed to pass through the upper surface 51 from the lower surface 52, and extends in an inward direction directed in the container 3. In the embodiment, the through-hole 60 of the bottom member 50 is formed at the deepest section of the container 3. Then, a central axis of the through-hole 60 of the bottom member 50 coincides with the axis C, and the through-hole 60 extends in the axis C direction.

As shown in FIG. 4, the base member 30, the plurality of annular members 40 and the bottom member 50 have surfaces opposite to the base member 30, the annular member 40 or the bottom member 50 adjacent thereto and extending in the communication direction the axis C direction) of the plurality of annular members 40. Specifically, the base member 30 has a surface 33, and the surface 33 is opposite to the neighboring annular members 40 and extends in the axis C direction. Similarly, the bottom member 50 has a surface 53, and the surface 53 is opposite to the neighboring annular members 40 and extends in the axis C direction.

The plurality of annular members 40 have surfaces 43 and surfaces 44. The surface 43 of the annular member 40 adjacent to the base member 30 is opposite to the surface 33 of the base member 30, and extends in the axis C direction. Then, the surface 44 of the annular member 40 is opposite to the surface 43 of the annular member 40 adjacent thereto, and extends in the axis C direction. Similarly, the surface 44 of the annular member 40 adjacent to the bottom member 50 is opposite to the surface 53 of the bottom member 50, and extends in the axis C direction. Then, the surface 43 of the annular member 40 is opposite to the surface 44 of the annular member 40 adjacent thereto, and extends in the axis C direction. The surfaces 43 and 44 of the other annular members 40 are opposite to the surfaces 44 and 43 of the annular members 40 adjacent thereto, and extend in the axis C direction.

A seal member (an O-ring) 70 is installed between the base member 30, the plurality of annular members 40 and the bottom member 50. Specifically, one seal member 70 is installed between the surface 33 of the base member 30 and the surface 43 of the annular member 40 adjacent to the base member 30, and in the embodiment, is accommodated in a groove formed in the surface 33 of the base member 30. The other separate seal member 70 is installed between the surface 53 of the bottom member 50 and the surface 44 of the annular member 40 adjacent to the bottom member 50, and in the embodiment, accommodated in a groove formed in the surface 53 of the bottom member 50. The other seal member 70 is installed between the surface 43 of the annular member 40 and the surface 44 of the annular member 40 adjacent thereto, and in the embodiment, accommodated in the groove formed in any one of the surfaces 43 and 44 opposite to each other.

Figure 5:
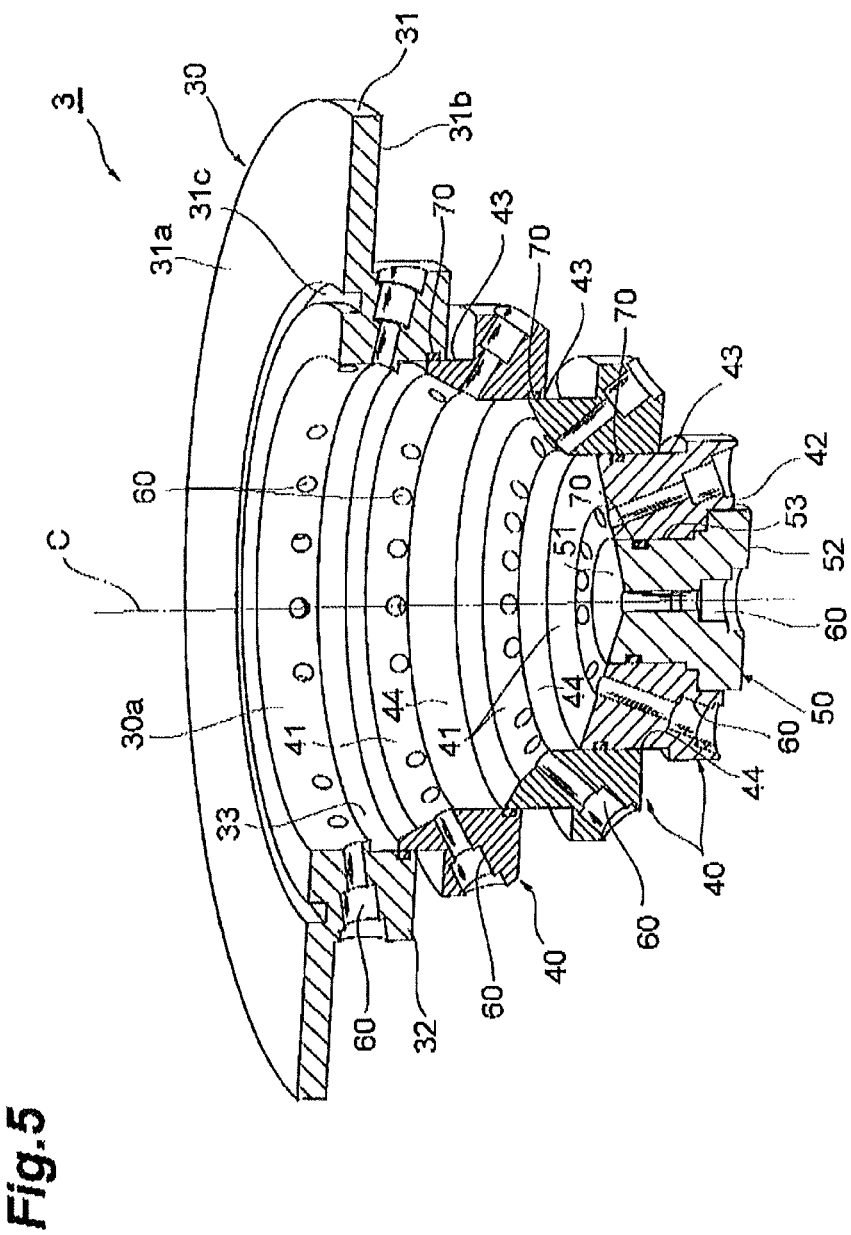
FIG. 5 is a view showing a situation of displacement of a plurality of annular members and a bottom member.

In the container 3 including the above-mentioned configuration, each of the annular members 40 and the bottom member 50 are configured to be relatively displaced in a communication direction (the axis C direction) with respect to the adjacent annular member 40 on the side of the base member 30 or the base member 30. FIG. 5 is a view showing such displacement. In FIG. 5, the annular member 40 adjacent to the base member 30 is displaced in the axis C direction with respect to the base member 30, and a distance between the annular member 40 and the base member 30 is increased. In addition, the bottom member 50 is displaced in the axis C direction with respect to the annular member 40 adjacent thereto, and a distance between the annular member 40 and the bottom member 50 is increased. Similarly, the other annular member 40 is displaced in the axis C direction with respect to the adjacent annular member 40 on the side of the base member 30, and a distance between the neighboring annular members 40 is increased. In this way, as the annular member 40 and the bottom member 50 are displaced in the axis C direction, a capacity of the container 3 is largely increased. As an interval between the inner circumferential surfaces 41 of the plurality of annular members 40 is increased, intervals between the plurality of optical fibers 11 disposed at one annular member 40 and the plurality of optical fibers 11 disposed at the other annular member 40 are increased.

As shown in FIG. 5, when each of the annular members 40 and the bottom member 50 are displaced, a step difference occurs in the inner surface of the container 3. The mammography device 1 may further include a spacer configured to bury the step difference and smoothly form the inner surface of the container 3. Accordingly, the boundary condition upon the image reconstruction can be simplified.

Figure 6:
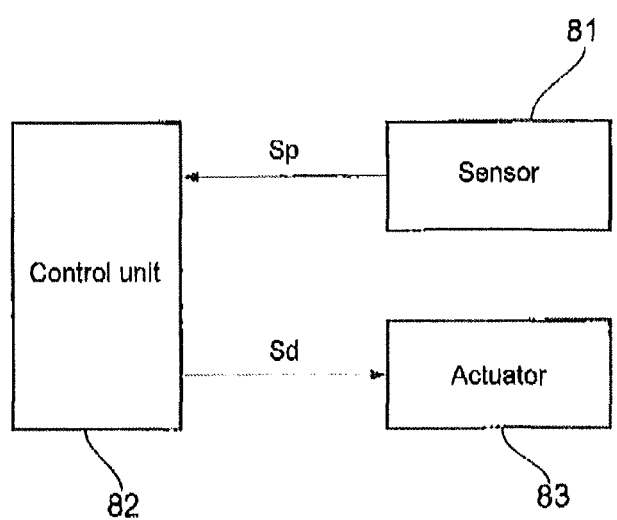
FIG. 6 is a block diagram showing a configuration configured to displace the annular members and the bottom member.

FIG. 6 is a block diagram showing a configuration for displacing each of the annular members 40 and the bottom member 50. As shown in FIG. 6, the mammography device 1 may further include a sensor 81, a control unit 82 and an actuator 83. That is, the sensor 81 detects positions in the axis C direction of each of the annular members 40 and the bottom member 50. The sensor 81 transmits a position signal Sp including information related to the positions of each of the annular members 40 and the bottom member 50 to the control unit 82. The control unit 82 transmits a driving signal Sd to the actuator 83 such that the capacity of the container 3 is increased to a desired size based on the position signal Sp. The actuator 83 displaces each of the annular members 40 and the bottom member 50 in response to the driving signal Sd.

In the embodiment, the control unit 82 continuously varies the depth of the container 3, i.e., the distance from the opening 30a of the base member 30 to the bottom member 50, or varies the distance in a plurality of predetermined steps. Here, the plurality of predetermined steps may be, for example, 2 steps, 3 steps, or 4 steps, and may be selected according to the shape or size of the breast B of the examinee A. For example, the distance from the opening 30a of the base member 30 to the bottom member 50 may be set to 3 steps (an S size, an M size and an L size). In this case, the depths of the container 3 of the S size, the M size and the L size may be, for example, 49 mm, 64 mm, and 86 mm. When the diameter of the opening 30a is, for example, 128 mm, the capacity of the container 3 becomes sizes of 425 cc, 559 cc, and 775 cc.

Effects obtained by the mammography device 1 according to the embodiment as described above will be described. In the mammography device 1, the container 3 to which the plurality of optical fibers 11 are attached has the plurality of annular members 40 and the bottom member 50, and each of the annular members 40 and the bottom member 50 are configured to be relatively displaced in the communication direction with respect to the adjacent member (the base member 30 or the annular member 40) on the side of the base member 30. According to the above-mentioned configuration, the inner capacity of the container 3 can be varied to match the shape or size (volume) of the breast B of the examinee A. In addition, since at least some of the plurality of optical fibers 11 is attached to the plurality of annular members 40, the positions of the plurality of optical fibers 11 are also varied with the displacement of the plurality of annular members 40.

Figure 7:
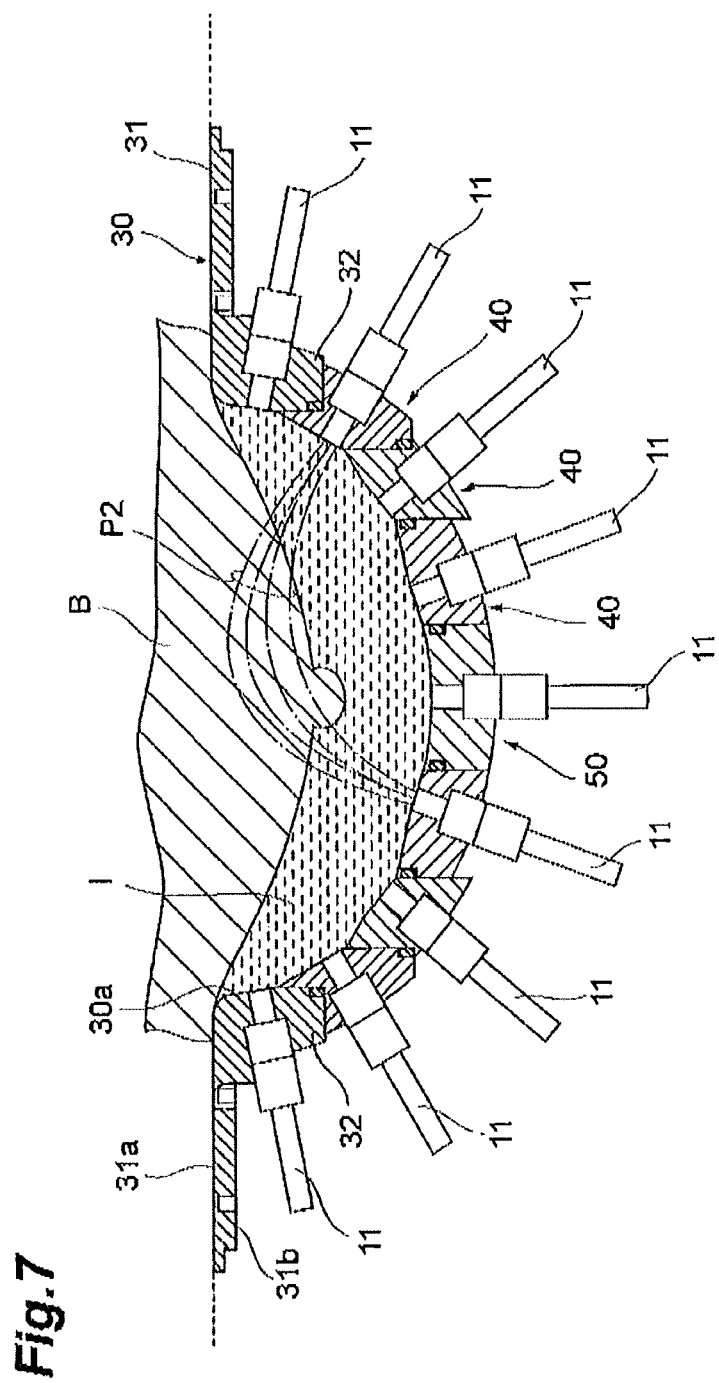
FIG. 7 is a cross-sectional view schematically showing a situation of radiation and detection of light with respect to the breast when a depth of the container is set to an S size.
Figure 8:
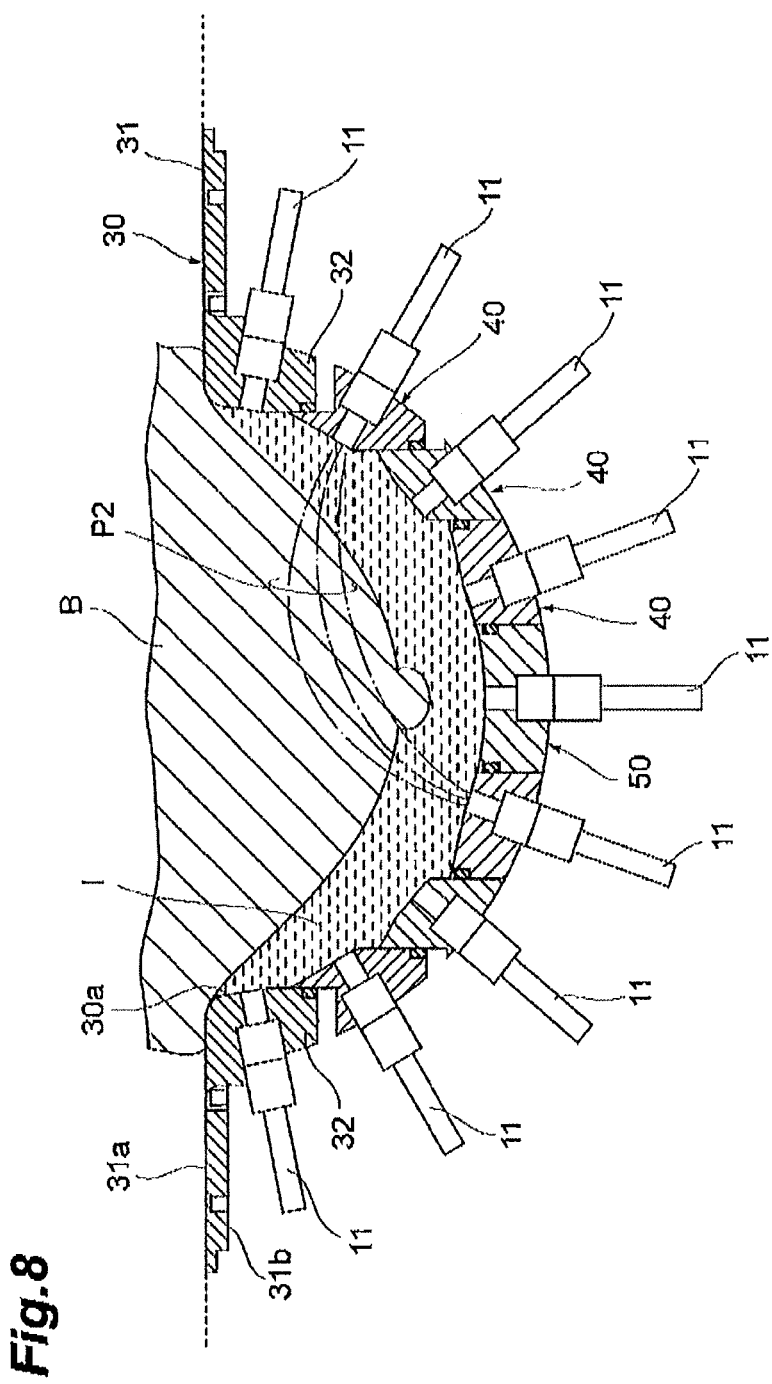
FIG. 8 is a cross-sectional view schematically showing a situation of radiation and detection of light with respect to the breast when a depth of the container is set to an M size.
Figure 9:
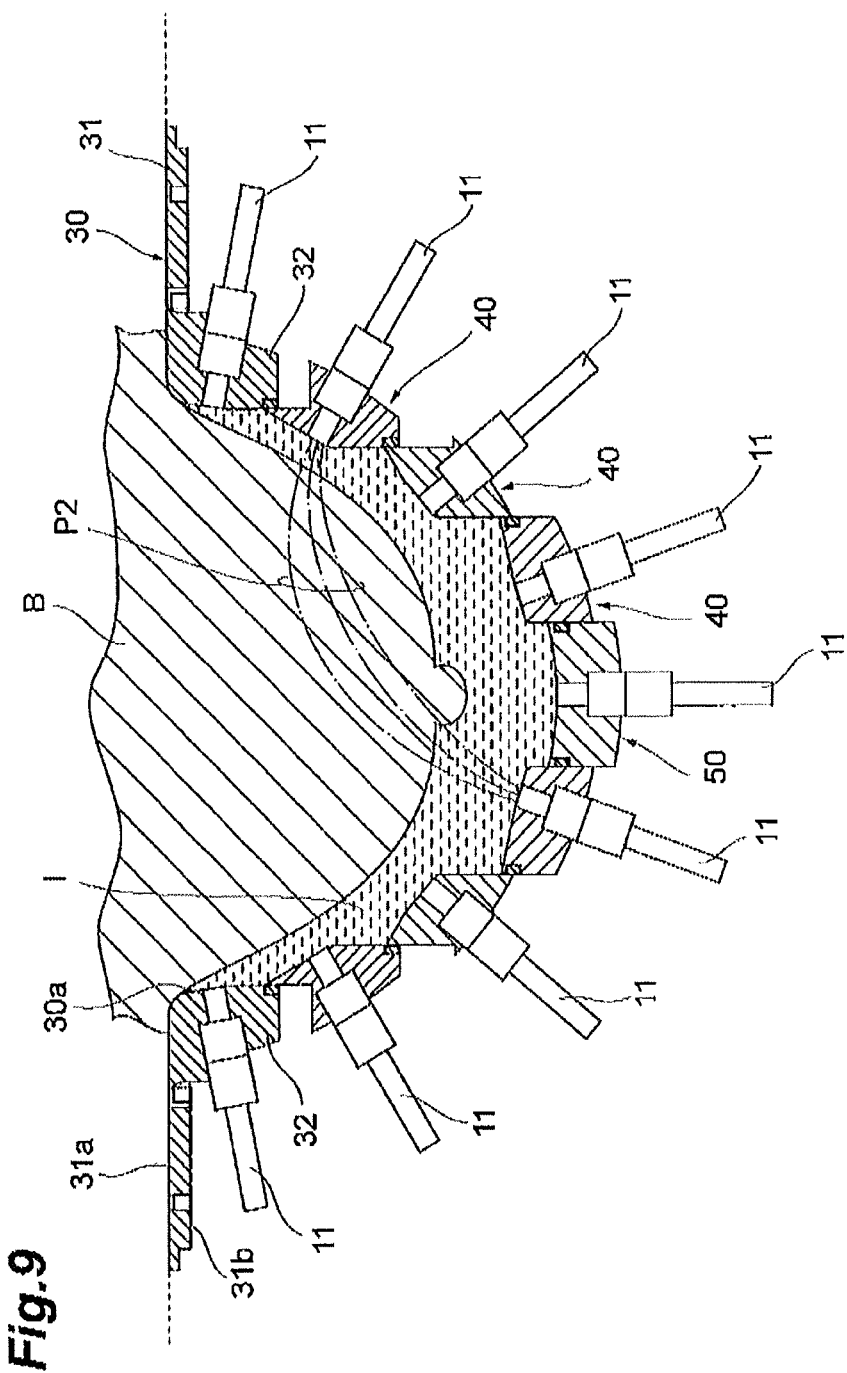
FIG. 9 is a cross-sectional view schematically showing a situation of radiation and detection of light with respect to the breast when a depth of the container is set to an L size.

Here, FIGS. 7 to 9 are cross-sectional views schematically showing situations of radiation and detection of light with respect to the breast B when the depth of the container 3 is set to the S size, the M size, and the L size. That is, FIG. 7 shows the case in which the depth of the container 3 is set to the S size, and the inner capacity of the container 3 is varied to match the relatively small breast B. FIG. 8 shows the case in which the depth of the container 3 is set to the M size, and the inner capacity of the container 3 is varied to match the breast B having an average size. FIG. 9 shows the case in which the depth of the container 3 is set to the L size, and the inner capacity of the container 3 is varied to match a relatively large breast B. As shown in the drawings, as the depth of the container 3 is varied, the distance between the breast B and each of the optical fibers 11 can be maintained substantially constantly regardless of the size of the breast B. In this way, according to the mammography device 1, a variation in distance between the plurality of optical fibers 11 and the breast B due to a difference in the shape and size of the breast B can be suppressed, and an amount of the pulse light P2 entering the breast B can be constantly maintained regardless of the size of the breast B. Accordingly, even when the breast B is relatively small, since a sufficient amount of internal information of the breast B is included in the detected diffused light, precision of the finally obtained internal information can be increased. That is, according to the mammography device 1, since an influence on precision of the internal information due to the difference in the shape or size of the breast B is reduced, image quality or resolution of the reconstructed image can be improved, image distortion can be reduced, and precision of the position information can be increased.

The diameter of the opening 30a of the base member 30 is mostly unrelated to the shape or size of the breast B. When the shape or size of the breast B differs, a distal end position of the breast B in the depth direction of the container 3 mainly varies. Accordingly, as the depth of the container 3 is varied as described in the embodiment, the above-mentioned effects can be appropriately obtained. In addition, while a configuration in which only the position of the optical fiber is varied while constantly maintaining the depth of the container may be considered, such a configuration is not preferable because the optical fiber may come in contact with the breast and deform the breast.

As described in the embodiment, the base member 30, the plurality of annular members 40 and the bottom member 50 may have the surfaces 33, 43, 44 and 53, respectively. As described above, in the mammography device 1, the gap between the container 3 and the breast is filled with the liquefied interface agent I. Here, as the base member 30, the plurality of annular members 40 and the bottom member 50 have surfaces opposite to the base member 30, the annular member 40 or the bottom member 50 adjacent thereto and extending in the communication direction, the neighboring members can be adhered to each other when the plurality of annular members 40 are disposed, and generation of the gap can be prevented.

As described in the embodiment, the seal members 70 may be installed between the base member 30 and the annular member 40 adjacent to the base member 30, between the neighboring annular members 40, and between the bottom member 50 and the annular member 40 adjacent to the bottom member 50. As the seal members 70 are installed between the surfaces thereof, leakage of the interface agent I from the container 3 can be appropriately prevented.

As described above, the control unit 82 may continuously vary the distance from the opening 30a of the base member 30 to the bottom member 50 (i.e., the depth of the container 3). Accordingly, since the capacity of the container 3 can be finely varied to match various shapes and sizes of the breast B, an influence on precision of the internal information due to the difference in the shape or size of the breast B can be further reduced.

Alternatively, as described in the embodiment, the control unit 82 may vary the distance from the opening 30a of the base member 30 to the bottom member 50 (i.e., the depth of the container 3) in the plurality of predetermined steps. In the mammography device 1, when the internal information of the breast B is acquired based on the detected diffused light from the breast B, the reconstructed image is calculated using the inner surface of the container 3 as the boundary condition. Here, when the capacity of the container 3 minutely differs among the examinees A, the boundary condition should be calculated at every time, and calculation of the reconstructed image takes a long time. On the other hand, like in the mammography device 1 of the embodiment, since the boundary condition is limited to the plurality of predetermined conditions as the control unit 82 varies the depth of the container 3 in the plurality of prescribed steps, the boundary condition need not be calculated at every measurement, and thus the calculation time of the reconstructed image can be reduced.

Like in the embodiment, some of the plurality of optical fibers 11 may be attached to the bottom member 50. The other fibers of the plurality of optical fibers 11 may be attached to the opening 30a of the base member 30. In this way, as some of the plurality of optical fibers 11 are attached to the member other than the plurality of annular members 40, the plurality of optical fibers 11 can be uniformly disposed around the breast B, precision of the internal information can be further increased.

Like in the embodiment, the plurality of optical fibers 11 are disposed at the plurality of respective annular members 40 in parallel in the circumferential direction, attachment angles of the plurality of optical fibers 11 with respect to the communication direction differ with respect to each of the plurality of annular members 40. Accordingly, at an angle according to the attachment position of the optical fiber 11, light can be precisely radiated toward the breast B. When each of the annular members 40 is disposed at a predetermined position (for example, a position of the M size), the angles of the plurality of optical fibers 11 with respect to the axis C may be set such that the optical axes of the plurality of optical fibers 11 installed at the annular members 40 across one point on the axis C.

(First Variant)

Figure 10:
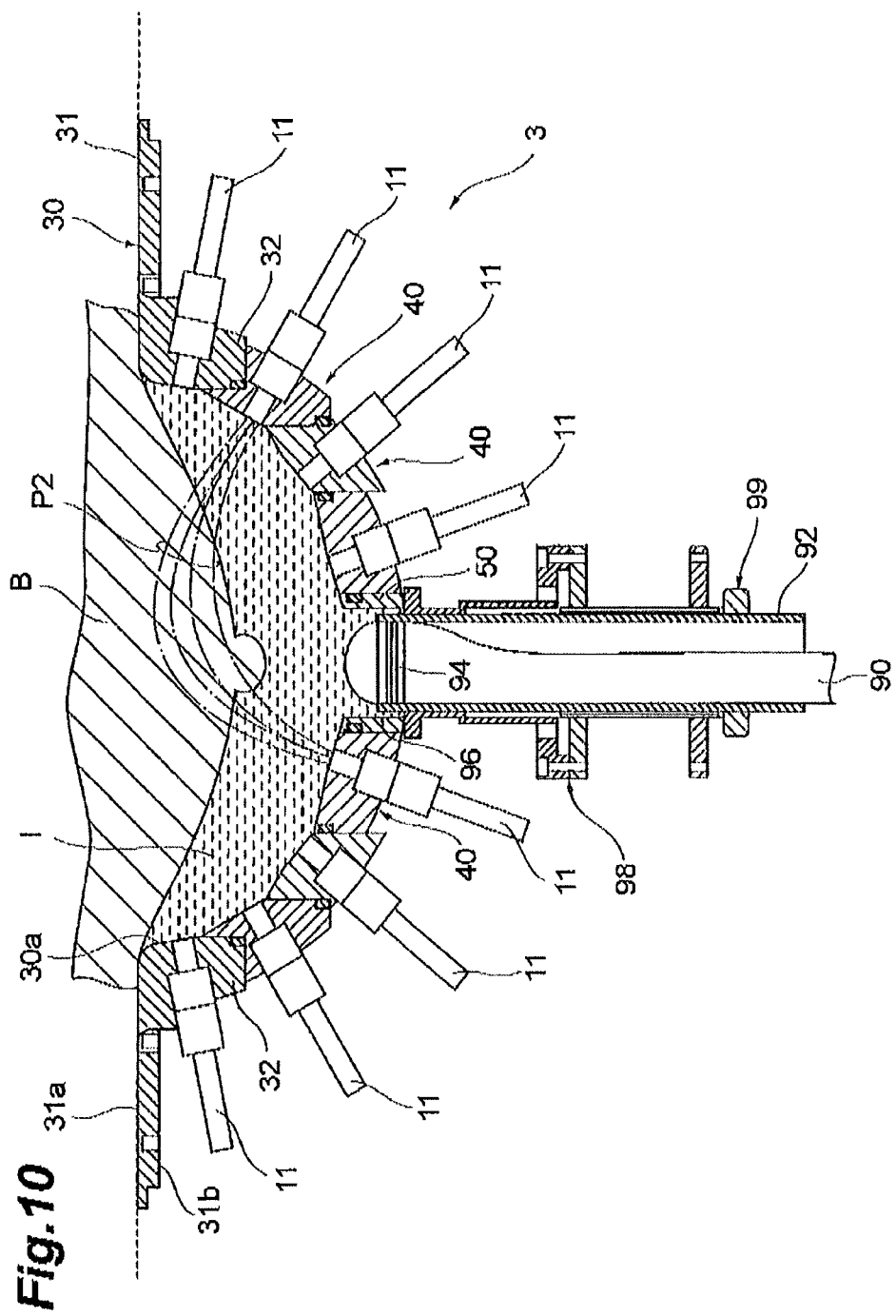
FIG. 10 is a cross-sectional view showing a configuration in the vicinity of the container serving as a first variant.

FIG. 10 is a cross-sectional view showing a configuration in the vicinity of the container 3 according to a first variant of the embodiment. A difference between the configuration of the variant and the embodiment is a bottom structure of the container. That is, in the variant, instead of the optical fiber, an ultrasonic wave probe (a probe) 90 is attached to a predetermined position (for example, the bottom member 50) of the container 3. The ultrasonic wave probe 90 is disposed to face inward in the container 3, scans ultrasonic waves toward the breast B, and receives the reflected waves from the breast B. The received signal is transmitted to, for example, the measurement apparatus 5 shown in FIG. 1. The measurement apparatus 5 generates an ultrasonic wave image of the breast B based on the received signal obtained from the ultrasonic wave probe 90.

In the variant, the ultrasonic wave probe 90 is inserted through a hole formed in the bottom member 50. The ultrasonic wave probe 90 is inserted into a cylindrical tube 92 and adhered to the inner surface of the tube 92 to prevent leakage of the interface agent I and to avoid interference with a scan radiation angle of the ultrasonic wave. A seal 94 configured to prevent the leakage of the interface agent I is installed between the tube 92 and the ultrasonic wave probe 90. A seal 96 configured to prevent the leakage of the interface agent I is installed between the tube 92 and the bottom member 50.

A vertically operating rotational ring 98 serving as a mechanism configured to vary the distance between the ultrasonic wave probe 90 and the breast B is installed around the tube 92 of the ultrasonic wave probe 90. The ultrasonic wave probe 90 is vertically moved by the vertically operating rotational ring 98. The ultrasonic wave probe 90 is positioned outside farther than the inner surface of the container 3 in the lowermost state, and is positioned inside further than the inner surface of the container 3 in the uppermost state. Further, a rotational operating ring 99 is installed around the tube 92 of the ultrasonic wave probe 90. The rotational operating ring 99 is a mechanism configured to rotate the ultrasonic wave probe 90 around an axis passing through the breast B.

As described in the variant, the mammography device may further include the ultrasonic wave probe 90. Accordingly, the ultrasonic wave image of the breast B is drafted, the distance from the opening 30a of the base member 30 to the bottom member 50 (i.e., the depth of the container 3), or disposition or capacity of the breast B in the container 3 can be previously checked, and the size of the container 3 can be complexly optimized to match the shape or size of the breast B. Accordingly, since the intensity of the signal from the breast B measured by the light is substantially equalized regardless of the size of the breast B, deviation between the reconstructed images can be reduced. Further, as the reconstructed image obtained by the optical measurement and the ultrasonic wave image are combined, a diagnosis image having a larger amount of information can be provided.

In addition, as described in the variant, the ultrasonic wave probe 90 may be attached to the bottom member 50. Accordingly, the ultrasonic wave can be radiated from a front surface of the breast B, and the ultrasonic wave image can be appropriately drafted.

(Second Variant)

Figure 11:
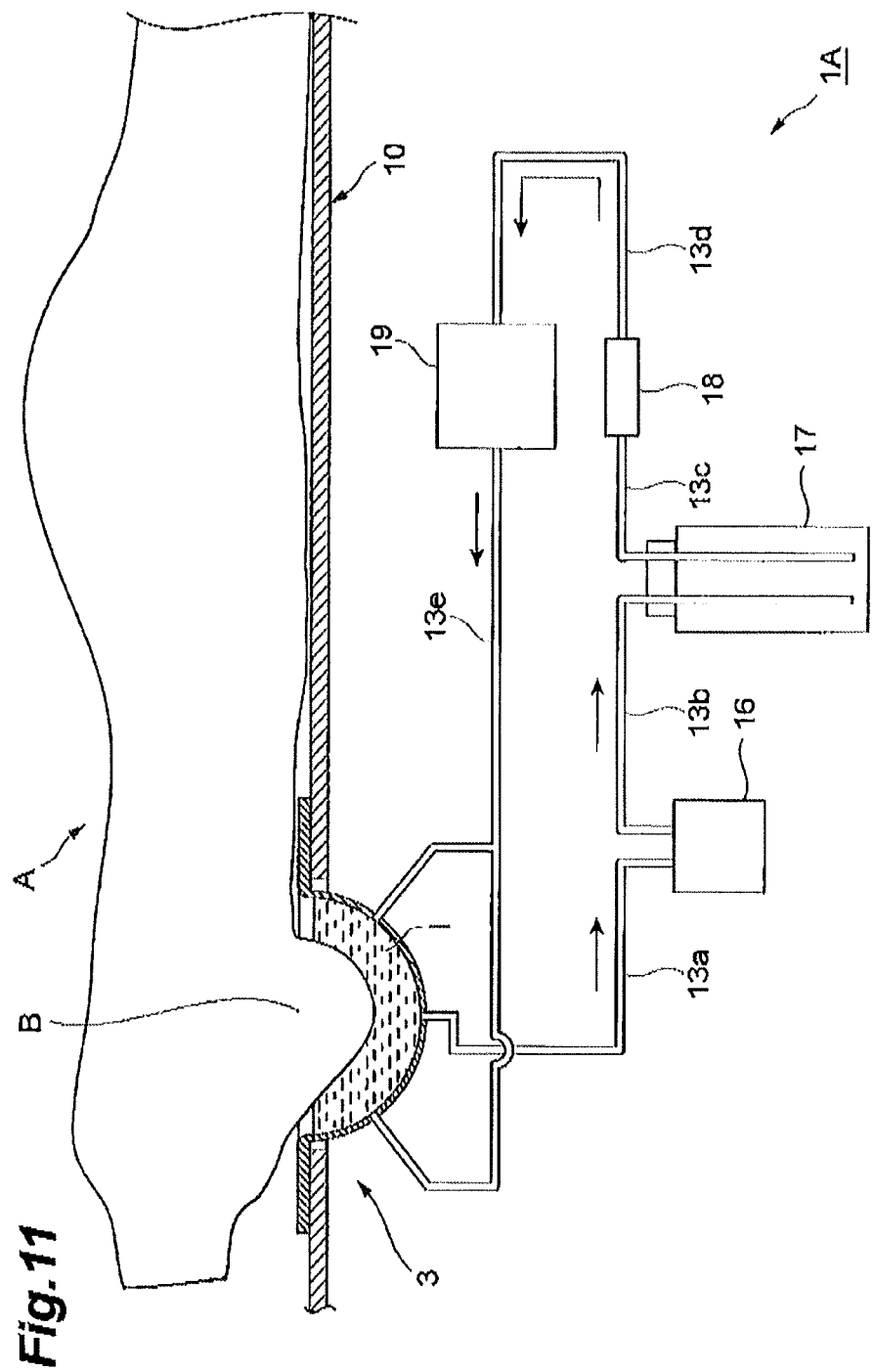
FIG. 11 is a view showing a configuration of a circulation system of an interface agent serving as a second variant.
Figure 12:
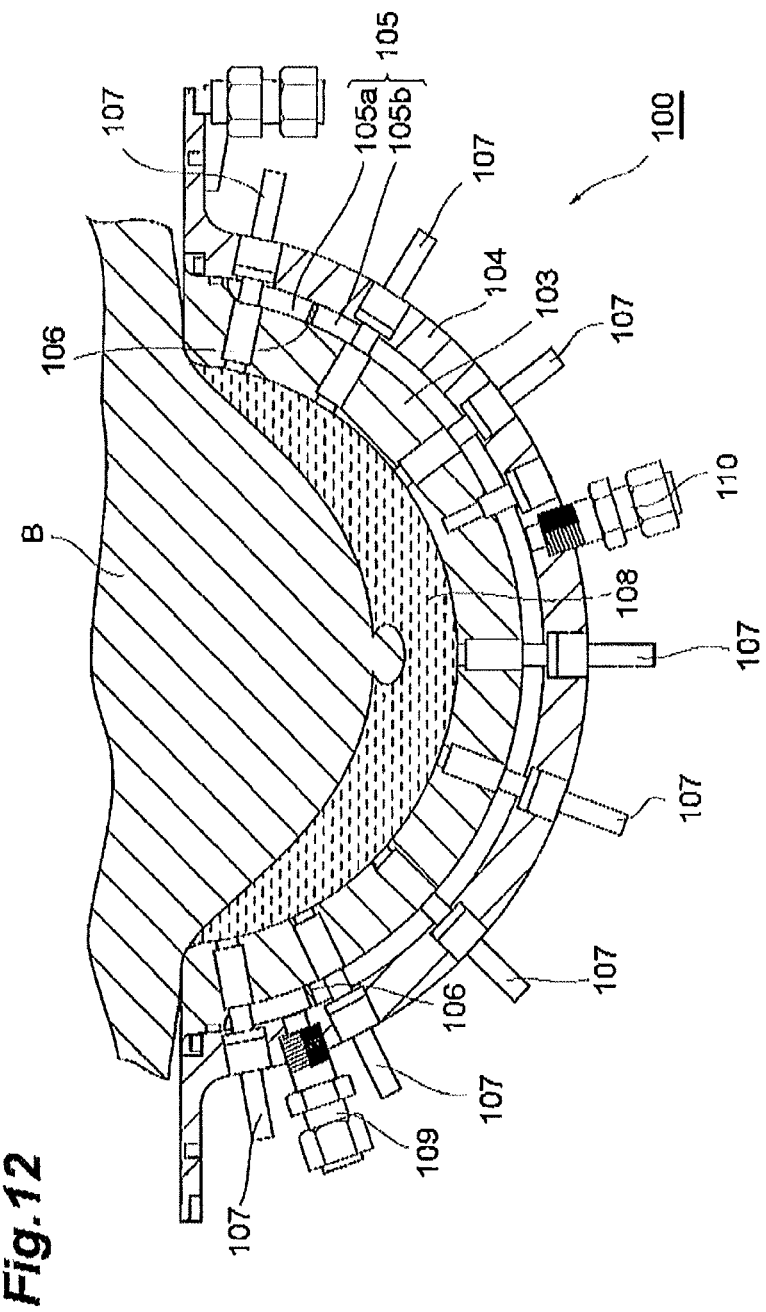
FIG. 12 is a cross-sectional view showing a configuration in the vicinity of a container of a mammography device disclosed in Patent Literature 1.
Figure 13:
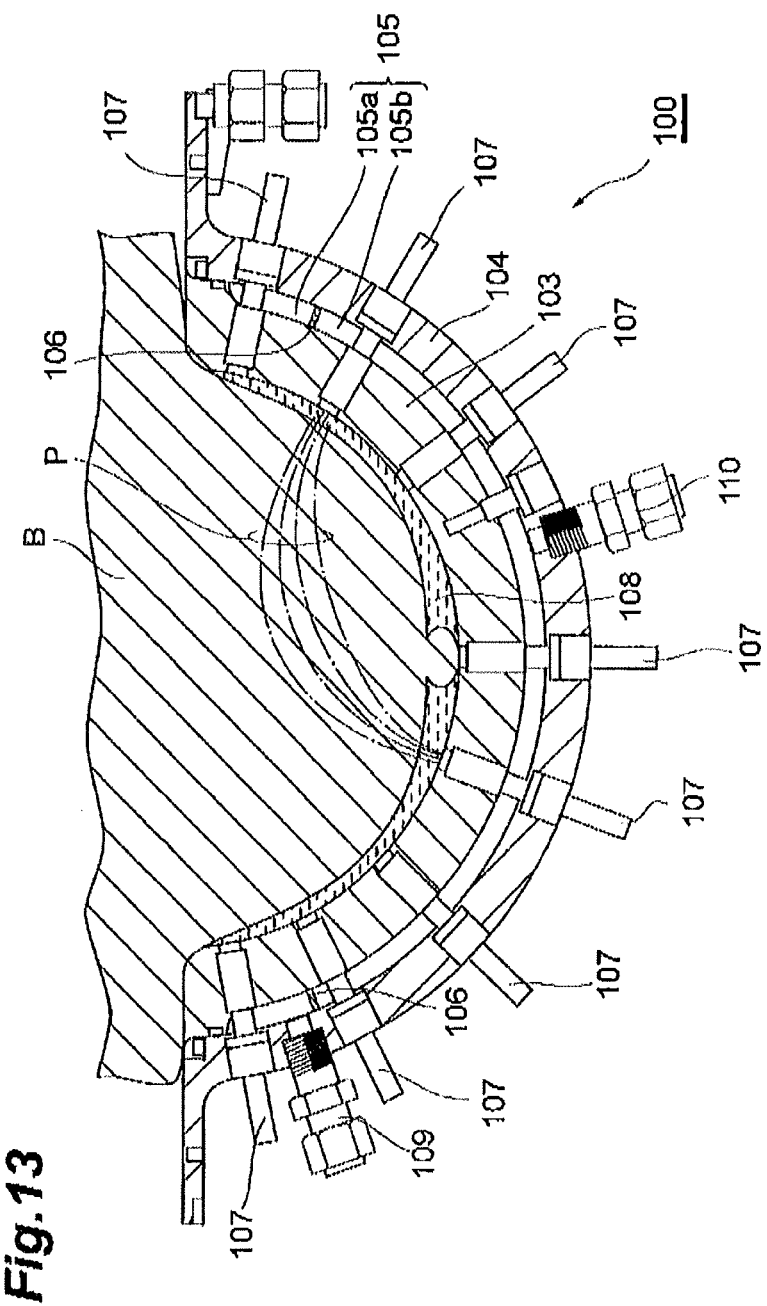
FIG. 13 is a view showing a situation of propagation of light when a volume of the breast is large.
Figure 14:
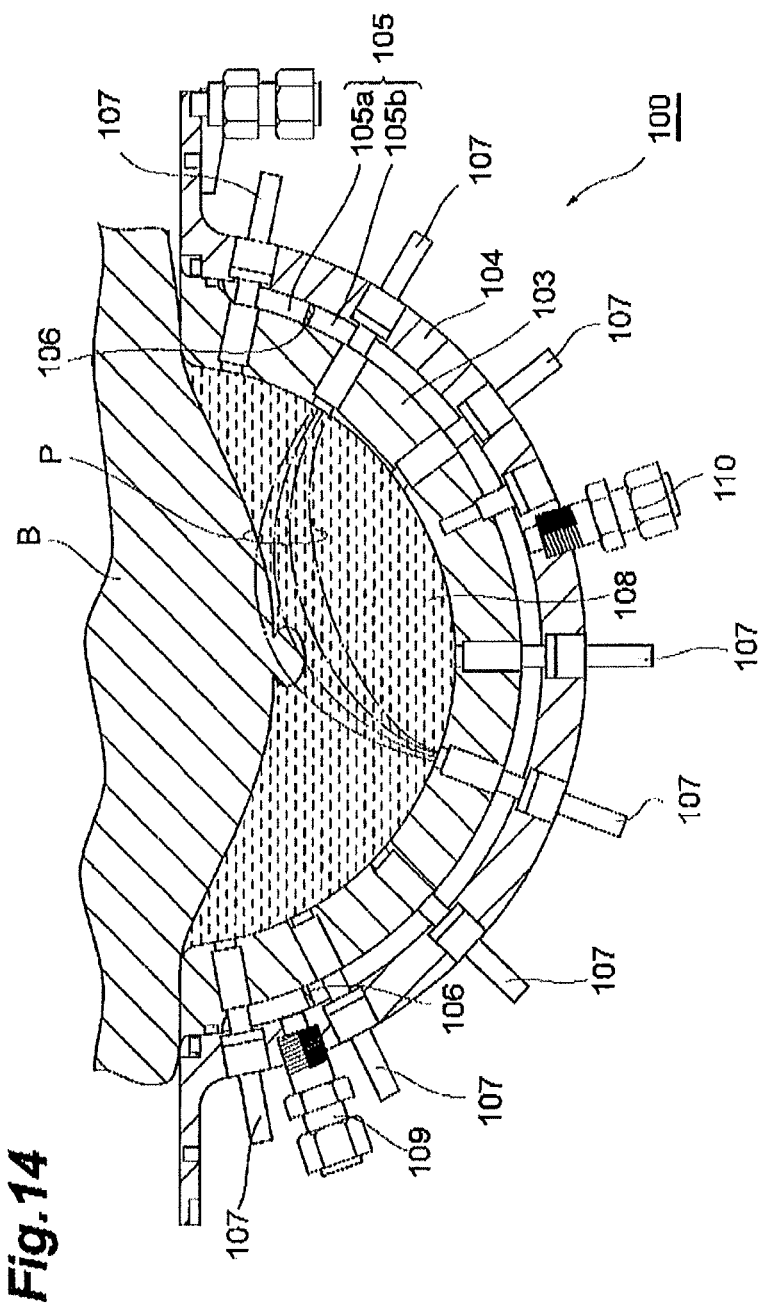
FIG. 14 is a view showing a situation of propagation of light when a volume of the breast is small.

FIG. 11 is a view showing a configuration of a circulation system 1A of an interface agent I according to a second variant of the embodiment. In FIG. 11, the container 3 is schematically shown. As shown in FIG. 2, the gap between the inner surface of the container 3 and the breast B is filled with the interface agent I. Since the boundary condition upon calculation by the calculation processing unit 25 can be fixed regardless of the size of the breast B as the optical coefficient between the breast B and the measurement optical fiber 11 is equalized to the breast B by the interface agent I, the internal information of the breast B can be more easily calculated. As the interface agent I, for example, a liquid formed by mixing a light scattering material (for example, Intralipid (trademark) or the like, which is a fat emulsion for intravenous injection) with pure water (for example, distilled water) at an appropriate ratio at which the light scattering coefficient coincides with that of the living body, or further mixing a light absorption material (for example, carbon ink or the like) at an appropriate ratio at which the light absorption coefficient coincides with that of the living body is appropriately used.

The Intralipid or carbon ink is hydrophobic. When the light scattering material or the light absorption material contained in the interface agent I has hydrophobicity, in the interface agent I in the container 3, the light scattering material or the light absorption material easily settles as time elapses. When these materials settle, the optical coefficient of the interface agent I becomes uneven, and detection precision of the transmitted diffusion light is decreased. Accordingly, the breast measurement apparatus of the variant further includes a circulation system 1A configured to prevent settlement of the light scattering material or the light absorption material and agitate the interface agent I outside the container 3 while circulating the interface agent I inside and outside the container 3.

As shown in FIG. 11, the circulation system 1A of the variant includes a circulation pump 16 configured to circulate the interface agent I, a tank 17 configured to store and agitate the interface agent I, a deaeration (degassing) apparatus 18 configured to remove air or bubbles melted in the interface agent I, and a heating apparatus 19 configured to heat the interface agent I. The interface agent I is heated and circulated by these apparatuses to prevent settlement and unevenness in the gantry. Since the bubbles of the interface agent I are removed by the deaeration apparatus 18, generation of optical distortion from the measurement light propagated in the interface agent can be prevented.

The circulation pump 16 is connected to the container 3 via a pipe 13a, and the interface agent I is suctioned into the circulation pump 16 from the container 3 through the pipe 13a. In addition, the circulation pump 16 is connected to the tank 17 via a pipe 13b, and the interface agent I is conveyed into the tank 17 through the pipe 13b. An agitator (not shown) is attached to the inside of the tank 17, and the stored interface agent I is agitated. The tank 17 is connected to the deaeration apparatus 18 via a pipe 13c, and the agitated interface agent I is conveyed to the deaeration apparatus 18 through the pipe 13c. The pressure of the interface agent I is reduced in the deaeration apparatus 18, and the bubbles and the melted gas element are removed. The deaeration apparatus 18 is connected to the heating apparatus 19 via a pipe 13d, and the degassed (and deaerated) interface agent I is conveyed to the heating apparatus 19 through the pipe 13d. Since the examinee A feels discomfort when the interface agent I is excessively cool, the interface agent I is heated in the heating apparatus 19 to about a body temperature. The heating apparatus 19 is connected to the container 3 via a pipe 13e, and the interface agent T is conveyed again to the container 3 through the pipe 13e. In this way, the interface agent I is circulated through the inside and the outside of the container 3 while being agitated. A connection sequence of the circulation pump 16, the tank 17, the deaeration apparatus 18, and the heating apparatus 19 may be varied and optimized according to necessity.

The mammography device according to the present invention is not limited to the above-mentioned embodiment but may be variously varied. For example, in the embodiment, while the container is exemplified as having a hemispherical shape, various shapes such as a conical shape, a columnar shape, and so on, may be applied to the container. In addition, in the embodiment, while the communication direction of the plurality of annular members (the displacement direction of the plurality of annular members) coincides with the central axis (axis C) direction of the plurality of annular members, the communication direction may be inclined with respect to the central axis of the annular member.

INDUSTRIAL APPLICABILITY

The present invention can be used for the mammography device capable of acquiring internal information of the breast by detecting intensity of the diffused light of the light radiated to the breast.

REFERENCE SIGNS LIST

1 . . . mammography device, 1A . . . circulation system, 3 . . . container, 4 . . . light source apparatus, 5 . . . measurement apparatus, 10 . . . bed, 11, 12 . . . optical fiber, 30 . . . base member, 31 . . . plate-shaped section, 32 . . . annular section, 40 . . . annular member, 50 . . . bottom member, 60 . . . through-hole, 70 . . . seal member, 81 . . . sensor, 82 . . . control unit, 83 . . . actuator, 90 . . . ultrasonic wave probe, A . . . examinee, B . . . breast, C . . . axis, I . . . interface agent, P1, P2 . . . pulse light, Sd . . . driving signal, Sp . . . position signal.

The invention claimed is:

1. A mammography device for acquiring internal information of a breast of an examinee by radiating light to the breast and detecting the diffused light, the mammography device comprising:
    a container configured to surround the breast, the container having a base member having an opening through which the examinee inserts the breast, a plurality of annular members continuously disposed at an opposite side of the examinee to come in communication with the opening, and a bottom member disposed inside the annular member spaced the farthest distance from the base member among the plurality of annular members; and
    a plurality of optical fibers attached to the container to be directed inward in the container and configured to perform radiation and detection of light,
    wherein an inner diameter of each of the annular members is smaller than that of the adjacent annular member on the side of the base member or that of the opening of the base member,
    wherein the annular members and the bottom member are configured to be relatively displaced in a communication direction with respect to the adjacent annular member on the side of the base member or the base member,
    wherein at least some of the plurality of optical fibers are attached to the plurality of annular members, and
    wherein the base member, the plurality of annular members, and the bottom member have opposite surfaces to the base member, the annular member, or the bottom member adjacent thereto, the opposite surfaces extending along the communication direction, and a plurality of o-rings are disposed between each of the opposite surfaces, the o-rings preventing leakage of a liquid interface agent disposed in an inner volume defined by an inner surface of base, inner surfaces of the plurality of annular members and an inner surface of the bottom member.

2. The mammography device according to claim 1, wherein o-rings are installed between the base member and the annular member adjacent to the base member, between the neighboring annular members, and between the bottom member and the annular member adjacent to the bottom member.

3. The mammography device according to claim 1, further comprising a control unit configured to control displacement in the communication direction of the plurality of annular members and the bottom member,
    wherein the control unit continuously varies a distance from the opening of the base member to the bottom member.

4. The mammography device according to claim 1, further comprising a control unit configured to control displacement in the communication direction of the plurality of annular members and the bottom member,
    wherein the control unit varies a distance from the opening of the base member to the bottom member in a plurality of predetermined steps.

5. The mammography device according to claim 1, further comprising an ultrasonic wave probe disposed to face inward in the container and configured to scan ultrasonic waves toward the breast and receive the reflected waves from the breast.

6. The mammography device according to claim 5, wherein the probe is attached to the bottom member.

7. The mammography device according to claim 1, wherein some of the plurality of optical fibers are attached to the bottom member.

8. The mammography device according to claim 1, wherein some of the plurality of optical fibers are attached to the opening of the base member.

9. The mammography device according to claim 1, wherein the plurality of optical fibers are disposed at the plurality of annular members in parallel in a circumferential direction, and
    attachment angles of the plurality of optical fibers with reference to the communication direction differ with respect to each of the plurality of annular members.

* * * * *